(12) United States Patent
Yap et al.

(10) Patent No.: US 11,504,393 B2
(45) Date of Patent: Nov. 22, 2022

(54) HYDROGEN SULFIDE SUSTAINED RELEASING DRESSING AND MANUFACTURING METHOD THEREOF

(71) Applicant: BenQ Materials Corporation, Taoyuan (TW)

(72) Inventors: Lie-Sian Yap, Taoyuan (TW); Chih-Yuan Chao, Taoyuan (TW); Yu-Pu Wang, Taoyuan (TW)

(73) Assignee: BenQ Materials Corporation, Taoyuan (TW)

( * ) Notice: Subject to any disclaimer, the term of this patent is extended or adjusted under 35 U.S.C. 154(b) by 10 days.

(21) Appl. No.: 16/705,199

(22) Filed: Dec. 5, 2019

(65) Prior Publication Data
US 2020/0237811 A1 Jul. 30, 2020

(30) Foreign Application Priority Data
Jan. 29, 2019 (TW) ................. 108103368

(51) Int. Cl.
| | | |
|---|---|---|
| *A61K 33/04* | (2006.01) | |
| *A61K 47/26* | (2006.01) | |
| *A61K 47/44* | (2017.01) | |
| *A61K 47/32* | (2006.01) | |
| *A61K 31/216* | (2006.01) | |
| *A61K 47/38* | (2006.01) | |
| *A61F 13/02* | (2006.01) | |
| *B29C 45/00* | (2006.01) | |
| *B29C 45/72* | (2006.01) | |
| *B29B 7/00* | (2006.01) | |
| *B29B 7/82* | (2006.01) | |
| *B29B 7/94* | (2006.01) | |
| *A61K 9/70* | (2006.01) | |
| *B29K 105/00* | (2006.01) | |
| *B29L 31/00* | (2006.01) | |
| *B29K 25/00* | (2006.01) | |
| *B29K 1/00* | (2006.01) | |

(52) U.S. Cl.
CPC .......... *A61K 33/04* (2013.01); *A61F 13/0289* (2013.01); *A61K 9/7007* (2013.01); *A61K 31/216* (2013.01); *A61K 47/26* (2013.01); *A61K 47/32* (2013.01); *A61K 47/38* (2013.01); *A61K 47/44* (2013.01); *B29B 7/005* (2013.01); *B29B 7/82* (2013.01); *B29B 7/94* (2013.01); *B29C 45/0001* (2013.01); *B29C 45/72* (2013.01); *B29K 2001/08* (2013.01); *B29K 2025/08* (2013.01); *B29K 2105/0035* (2013.01); *B29K 2105/0064* (2013.01); *B29L 2031/753* (2013.01)

(58) Field of Classification Search
None
See application file for complete search history.

(56) References Cited

U.S. PATENT DOCUMENTS

| | | | |
|---|---|---|---|
| 2013/0102947 A1* | 4/2013 | Auguste | A61F 13/0233 602/54 |
| 2018/0221210 A1 | 8/2018 | Willey et al. | |
| 2018/0271789 A1* | 9/2018 | Sung | A61K 33/04 |

FOREIGN PATENT DOCUMENTS

| | | |
|---|---|---|
| CN | 1418114 A | 5/2003 |
| TW | 201834637 A | 10/2018 |

* cited by examiner

*Primary Examiner* — Patricia Duffy
*Assistant Examiner* — Garen Gotfredson
(74) *Attorney, Agent, or Firm* — CKC & Partners Co., LLC

(57) ABSTRACT

The invention is to provide a hydrogen sulfide sustained releasing dressing and a manufacturing method thereof. The hydrogen sulfide sustained releasing dressing includes a hydrocolloid, a surfactant and sodium hydro sulfide. The manufacturing method includes (a) heating and stirring a hydrocolloid material; (b) adding a surfactant and sodium hydrosulfide into the hydrocolloid material; and (c) injecting the hydrocolloid material containing the surfactant and the sodium hydrosulfide into a mold for thermoforming a hydrogen sulfide sustained releasing dressing.

10 Claims, No Drawings

HYDROGEN SULFIDE SUSTAINED RELEASING DRESSING AND MANUFACTURING METHOD THEREOF

CROSS-REFERENCE TO RELATED APPLICATION

This application claims the priority benefit of Taiwanese application serial No. 108103368, filed on Jan. 29, 2019, which is incorporated herein by reference.

BACKGROUND OF THE INVENTION

Field of the Invention

The present invention is related to a hydrogen sulfide sustained releasing dressing and a manufacturing method thereof, especially related to a hydrogen sulfide sustained releasing dressing which can sustained release hydrogen sulfide gas to improve the chronic wound healing and a manufacturing method thereof.

Description of Related Art

Hydrogen sulfide ($H_2S$) is the third discovered endogenous gaseous transmitter following nitric oxide and carbon monoxide. By the animal experimentation, it has been proved that hydrogen sulfide gas has several efficacies such as vasodilation, inhibition of vascular smooth muscle cell proliferation, induction of vascular smooth muscle cell apoptosis, improving vascular endothelial cell proliferation, anti-inflammatory and antioxidation. It has been known in the prior art that cells can slowly produce extreme low concentration of hydrogen sulfide gas. However, an external donor of hydrogen sulfide cannot truly simulate the producing rate of hydrogen sulfide in the human body.

Sodium hydrosulfide (NaHS) can be used as a donor of hydrogen sulfide gas because the hydrogen sulfide gas will be released when sodium hydrosulfide is dissolved in water. However, the reaction that sulfide ion ($HS^-$) from sodium hydrosulfide combines with hydrogen ion ($H^+$) in water to release hydrogen sulfide gas is very fast, thereby the high concentration of the hydrogen sulfide gas is released in a short period of time. The high concentration of hydrogen sulfide is toxic for cells which will induce adverse reactions such as cell apoptosis or inflammatory. Although the low concentration of hydrogen sulfide has efficacies for wound healing, the medical application of hydrogen sulfide is limited due to the toxicity of the high concentration of hydrogen sulfide.

Therefore, there is a need to provide a dressing which can sustained release hydrogen sulfide and will not generate cytotoxicity in order to improve wound healing.

SUMMARY OF THE INVENTION

The present invention provides a novel hydrogen sulfide sustained releasing dressing and a novel manufacturing method thereof. The hydrogen sulfide sustained releasing dressing of the present invention can sustained release hydrogen sulfide and does not generate cytotoxicity; thereby the chronic wound healing is improved efficiently.

In one aspect of the present invention, provided is a hydrogen sulfide sustained releasing dressing comprising a hydrocolloid, a surfactant, and sodium hydrosulfide.

In an embodiment of the present invention, the hydrocolloid is present at an amount of 60 to 140 parts by weight, the surfactant is present at an amount of 0.2 to 2 parts by weight, and the sodium hydrosulfide is present at an amount of 0.1 to 0.5 parts by weight.

In an embodiment of the present invention, the surfactant is polysorbate 80, polysorbate 20, polysorbate 60, or polysorbate 40.

In an embodiment of the present invention, the hydrocolloid comprises an elastomer, a hydrophilic polymer, a tackifier, and an extender.

In an embodiment of the present invention, the elastomer is present at an amount of 10 to 30 parts by weight, the hydrophilic polymer is present at an amount of 20 to 60 parts by weight, the tackifier is present at an amount of 20 to 60 parts by weight, and the extender is present at an amount of 2 to 20 parts by weight.

In an embodiment of the present invention, the elastomer is selected from at least one of the group consisting of styrene-isoprene-styrene (SIS) copolymer, styrene-butadiene-styrene (SBS) copolymer, styrene-(ethylene-butylene)-styrene (SEBS) copolymer and styrene-(ethylene-propylene)-styrene (SEPS) copolymer, or a combination thereof.

In an embodiment of the present invention, the hydrophilic polymer is selected from at least one of the group consisting of sodium carboxymethyl cellulose, hydroxyethyl cellulose, sodium alginate, gelatin, pectin, carboxymethyl chitosan, guar gum, locust bean gum, collagen and karaya gum, or a combination thereof.

In an embodiment of the present invention, the tackifier is at least one selected from the group consisting of abietic resin, terpene resin, C5 petroleum resin, C9 petroleum resin and high-purity dicyclopentadiene (H-DCPD), or a combination thereof.

In an embodiment of the present invention, the extender is mineral oil, liquid paraffin, castor oil, dibutyl phthalate, lanolin and naphthenic oil, or a combination thereof.

In an embodiment of the present invention, the hydrocolloid comprises an antioxidant ranging from 0.2 to 2 parts by weight.

In an embodiment of the dressing of the present invention, the antioxidation is hindered phenol, thiosynergist, phosphite or secondary aromatic amine.

In another aspect of the present invention, provided is a manufacturing method for hydrogen sulfide sustained releasing dressing, comprising the steps of: (a) heating and stirring a hydrocolloid material; (b) adding a surfactant and sodium hydrosulfide into the hydrocolloid material; and (c) injecting the hydrocolloid material containing the surfactant and sodium hydrosulfide into a mold for thermoforming a hydrogen sulfide sustained releasing dressing.

In an embodiment of the manufacturing method of the present invention, the hydrocolloid material is present at an amount of 60 to 140 parts by weight, the surfactant is present at an amount of 0.2 to 2 parts by weight, and the sodium hydrosulfide is present at an amount of 0.1 to 0.5 parts by weight.

In an embodiment of the manufacturing method of the present invention, a heating temperature in the step of (a) ranges from 100° C. to 200° C.

In an embodiment of the manufacturing method of the present invention, a heating time in the step of (a) ranges from 1 hour to 1.5 hours.

In an embodiment of the manufacturing method of the present invention, the step of (b) further comprises a heating treatment, the heating treatment is conducted at a temperature ranging from 100° C. to 150° C.

In an embodiment of the manufacturing method of the present invention, the heating time is ranging from 15 minutes to 45 minutes.

The above and other aspects of the invention will become better understood with regard to the following detailed description of the preferred but non-limiting embodiment(s). These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be affected without departing from the spirit and scope of the novel concepts of the disclosure.

DETAILED DESCRIPTION OF THE INVENTION

In the following detailed description, for purposes of explanation, numerous specific details are set forth in order to provide a thorough understanding of the disclosed embodiments. It will be apparent, however, that one or more embodiments may be practiced without these specific details.

An object of the present invention is to provide a hydrogen sulfide sustained releasing dressing, which comprises a hydrocolloid, a surfactant and sodium hydrosulfide. The hydrogen sulfide sustained releasing dressing of the invention can avoid the problem of cytotoxicity due to a high concentration of hydrogen sulfide releasing in a short period of time. Therefore, the chronic wound healing can be improved effectively. According to the hydrogen sulfide sustained releasing dressing of the present invention, the concentration of hydrogen sulfide is less than 1300 µM in the released process, preferably ranging from 1 µM to 1000 µM, and more preferably ranging from 1 µM to 500 µM.

In an embodiment of the hydrogen sulfide sustained releasing dressing of the present invention, the hydrocolloid can be present at an amount of 60 to 140 parts by weight, the surfactant can be present at an amount of 0.2 to 2 parts by weight, and the sodium hydrosulfide can be present at an amount of 0.1 to 0.5 parts by weight. When the amount of sodium hydrosulfide is excessive, the concentration of the released hydrogen sulfide gas will be too high and results in cytotoxicity. When the amount of sodium hydrosulfide is insufficient, the concentration of the released hydrogen sulfide gas is too low to improve wound healing effectively.

Suitable hydrocolloid can be a known hydrocolloid composition for dressings. The hydrocolloid has the ability to absorb the wound exudate. After the absorption of the wound exudate, the hydrophilic materials in the hydrocolloid can form a semisolid substance like a sol-gel and attach to the wound bed, providing and maintaining a wet environment which is conductive to wound healing. Furthermore, due to its adhesiveness, the hydrocolloid can form an occlusive surface of the wound to enhance the capillary proliferation and granulation tissue formation, accelerating the wound healing. Because the hydrocolloid dressing can provide a closed environment to facilitate the macrophages to remove the necrotic tissue, the hydrocolloid also has the efficacy of debridement. In an embodiment of the present invention, the hydrocolloid can comprise an elastomer, a hydrophilic polymer, a tackifier and an extender.

The function of the elastomer is mainly to provide formability, viscosity and softness. The elastomer is a hydrophobic structure and can avoid sodium hydrosulfide to directly contact with water by cladding sodium hydrosulfide with the elastomer, thereby the released rate of hydrogen sulfide can be slowed down and controlled. Suitable elastomer can be, for example, styrene-isoprene-styrene (SIS) copolymer, styrene-butadiene-styrene (SBS) copolymer, styrene-(ethylene-butylene)-styrene (SEBS) copolymer and styrene-(ethylene-propylene)-styrene (SEPS) copolymer, or a combination thereof, but not limited thereto.

The hydrophilic polymer has an ability to absorb liquid and can swell rather than dissolve after the absorption of the exudate due to have a crosslink structure, so as to be used to provide the property of the water absorption. Suitable hydrophilic polymer comprises natural, synthetic or semi-synthetic hydrophilic polymer. The natural hydrophilic polymer comprises, for example, polysaccharide polymer such as pectin, gum arabic, guar gum, agar, starch, xanthan gum and dextran; protein; or peptide polymer such as gelatin, albumin and casein. Semi-synthetic hydrophilic polymer comprises, for example, carboxymethyl cellulose, sodium carboxymethyl cellulose, methyl cellulose, ethyl cellulose, hydroxyethyl cellulose, hydroxypropyl cellulose, methyl hydroxypropyl cellulose, sodium alginate and carboxymethyl starch. Synthetic hydrophilic polymer comprises, for example, acrylic polymer (such as poly(acrylic acid) and polyacrylamide), poly vinyl alcohol, polyvinyl pyrrolidone, polyethylene glycol and poly vinyl methyl ether. In the preferred embodiment of the present invention, the hydrophilic polymer can be at least one of sodium carboxymethyl cellulose, hydroxyethyl cellulose, odium alginate, gelatin, pectin, carboxymethyl chitosan, guar gum, locust bean gum, collagen and karaya gum, or a combination thereof, but not limited thereto. When the amount of the hydrophilic polymer is excessive, the water absorption rate of the hydrocolloid will be too fast and causing the released rate of the hydrogen sulfide to be too fast, which results in cytotoxicity. When the amount of the hydrophilic polymer is insufficient, the water absorption rate is too slow and causing the released rate of the hydrogen sulfide gas too slow to improve wound healing effectively.

The tackifier can be used to further adjust the viscosity of the hydrocolloid. Suitable tackifier can be at least one of abietic resin, terpene resin, C5 petroleum resin, C9 petroleum resin and high-purity dicyclopentadiene (H-DCPD), or a combination thereof.

The extender can provide wetting and/or viscosity controlling. Suitable extender is at least one of mineral oil, liquid paraffin, castor oil, dibutyl phthalate, lanolin, and naphthenic oil, or a combination thereof.

In an embodiment of the present invention, the elastomer can be present at the amount of 10 to 30 parts by weight, the hydrophilic polymer can be present at the amount of 20 to 60 parts by weight, the tackifier can be present at the amount of 20 to 60 parts by weight, and the extender can be present at the amount of 2 to 20 parts by weight in the hydrocolloid of this embodiment.

In another embodiment of the present invention, the hydrocolloid can selectively further comprise 0.2 to 2 parts by weight of an antioxidant to prevent the properties changed due to the aging of the elastomer. Suitable antioxidant can be hindered phenol, thiosynergist, phosphite or secondary aromatic amine.

The hydrophilic polymer is dispersed in the elastomer. With the addition of the surfactant, its hydrophilic ends can wet the surface of the hydrocolloid after the contact to water; so that the hydrophilic polymer becomes swelling and absorbs the wound exudate, to promote water molecules penetrating into the hydrophobic elastomer. Therefore, the hydrocolloid can have different water absorption rates by adjusting the amount ratio of the hydrophilic polymer and the surfactant, such that the hydrogen sulfide cladded by the hydrocolloid has different the released rate of hydrogen sulfide depending on the water absorption rate of the hydrocolloid. In an embodiment of the present invention, the surfactant can be polysorbate 80, polysorbate 20, polysorbate 60 or polysorbate 40. When the amount of the surfactant is excessive, the absorption rate of the hydrocolloid is too fast and causing the released concentration of hydrogen sulfide is too high. When the amount of the surfactant is insufficient, the absorption rate of the hydrocolloid is too slow and affecting the released rate of the hydrogen sulfide.

Another aspect of the present invention further provides a manufacturing method for hydrogen sulfide sustained releasing dressing, comprising but not limited to the following steps.

First, in the step of (a), a hydrocolloid material is heated and stirred. In an embodiment of the manufacturing method of the present invention, the hydrocolloid material can be present at an amount of 60 to 140 parts by weigh, and the hydrocolloid material can comprise, for example, an elastomer, a hydrophilic polymer, a tackifier and an extender. In the preferred embodiment of the manufacturing method of the present invention, the heating temperature can be ranging from 100° C. to 200° C. and the heating time can be ranging from 1 hour to 1.5 hours in the step of (a).

Then, in the step of (b), the surfactant and sodium hydrosulfide are added into the hydrocolloid material. The amount of the surfactant can be 0.2 to 2 parts by weight, and the amount of sodium hydrosulfide can be 0.1 to 0.5 parts by weight. In the preferred embodiment of the manufacturing method of the present invention, the method can further comprise a heating treatment in the step of (b), wherein the heating temperature is ranging from 100° C. to 150° C., and the heating time is ranging from 15 minutes to 45 minutes.

Finally, in the step of (c), the hydrocolloid material containing the surfactant and sodium hydrosulfide is injected into a mold to thermoform a hydrogen sulfide sustained releasing dressing. The thermoforming temperature is, for example, ranging from 50° C. to 100° C.

The following Examples are used to further describe the present invention rather than to limit thereto.

EXAMPLE

Example 1

15.4 g of styrene-isoprene-styrene (SIS) copolymer (Kraton D1161, available from Kraton, USA), 36.55 g of C9 modified resin (Wingtack 86, available from CRAY VALLEY, USA), 6.4 g of mineral oil (Kaydol white mineral oil, available from Sonneborn, USA) and 1 g of hindered phenol of pentaerythritol tetrakis (3-(3,5-di-tert-butyl-4-hydroxyphenyl)propionate) (Chinox 1010, available from DOUBLE BOND CHEMICAL, Taiwan) were stirred for 60 minutes in a nitrogen atmosphere at a temperature of 180° C. to form a mixture. After the temperature decreasing down to 120° C., 40 g of sodium carboxymethyl cellulose, 0.5 g of surfactant of Tween 80, and 0.15 g of sodium hydrosulfide were added into the mixture and stirred for 10 minutes, and then the mixture was injected into a mold to thermoform at a temperature of 90° C. to obtain a hydrogen sulfide sustained releasing dressing.

Example 2

The steps and the raw materials in Example 2 were same as Example 1, except that 36.5 g of C9 modified resin was used instead of 36.55 g of C9 modified resin, and 0.2 g of sodium hydrosulfide was used instead of 0.15 g of sodium hydrosulfide.

Example 3

The steps and the raw materials in Example 3 were same as Example 1, except that 15.3 g of styrene-isoprene-styrene (SIS) copolymer was used instead of 15.4 g of styrene-isoprene-styrene (SIS) copolymer, 36.3 g of C9 modified resin was used instead of 36.55 g of C9 modified resin, and 0.5 g of sodium hydrosulfide was used instead of 0.15 g of sodium hydrosulfide.

Example 4

The steps and the raw materials in Example 4 were same as Example 1, except that 17.93 g of styrene-isoprene-styrene (SIS) copolymer was used instead of 15.4 g of styrene-isoprene-styrene (SIS) copolymer, 42.59 g of C9 modified resin was used instead of 36.55 g of C9 modified resin, 30 g of sodium carboxymethyl cellulose is used instead of 40 g of sodium carboxymethyl cellulose, and 0.5 g of sodium hydrosulfide was used instead of 0.15 g of sodium hydrosulfide.

Comparative Example 1

The steps and the raw materials in Comparative Example 1 were same as Example 1, except that 15.2 g of styrene-isoprene-styrene (SIS) copolymer was used instead of 15.4 g of styrene-isoprene-styrene (SIS) copolymer, 36 g of C9 modified resin was used instead of 36.55 g of C9 modified resin, and 1 g of sodium hydrosulfide was used instead of 0.15 g of sodium hydrosulfide.

The released rates of the hydrogen sulfide of the hydrogen sulfide sustained releasing dressing in Examples 1 to 4 and Comparative Example 1 were measured by methylene blue method.

Firstly, a calibration curve was built by standard samples with identified concentration. The calibration curve was prepared as following: 500 μL of phosphate buffered solution (pH=7.4) containing 0.04 mg/mL sodium hydrosulfide was prepared and diluted to the identified concentration for the series of standard samples. A phosphate buffered solution without sodium hydrosulfide was prepared as well. 100 μL of each standard sample was mixed with 100 μL of 1.0 wt % zinc acetate solution and then 20 μL of 20 mM N,N-dimethyl-p-phenylenediamine sulfate in 7.2 N hydrogen chloride solution and 20 μL of 30 mM of ferric chloride (FeCl$_3$) in 1.2 N of hydrogen chloride solution were added to react for 10 minutes. The ferric chloride was used as an oxidant to catalyze the reaction of N,N-dimethyl-p-phenylenediamine sulfate with hydrogen sulfide generated from sodium hydrosulfide dissolved in water to produce methylene blue. The methylene blue calibration curve was built by measuring the absorption of methylene blue at wavelength of 670 nm and thus, the concentration of the hydrogen sulfide can be calculated according to the calibration curve. The results were shown in the following Table 1.

The dressings obtained from Examples 1 to 4 and Comparative Example 1 were placed into 1500 μL of phosphate buffered solution and stood for 2 hours, 4 hours, 6 hours, 8 hours, 18 hours, 24 hours, 42 hours and 48 hours respectively. In 100 μL of the phosphate buffered solution in which the dressing soaked, 100 μL of 1.0 wt % zinc acetate solution, 20 μL of 20 mM N,N-dimethyl-p-phenylenediamine sulfate in 7.2 N of hydrogen chloride solution, and 20 µL of 30 mM of ferric chloride in 1.2 N hydrogen chloride solution were added to react for 20 minutes. Then, the absorption of methylene blue at wavelength of 670 nm was measured to calculate the concentration of the hydrogen sulfide in each sample of the Examples. The results were shown in the following Table 1.

TABLE 1

The results in Examples 1 to 4 and Comparative Example 1

| Time (hour) | Example 1 [µM] | Example 2 [µM] | Example 3 [µM] | Example 4 [µM] | Comparative Example 1 [µM] |
|---|---|---|---|---|---|
| 2 | 252.3921 | 246.6588 | 922.31 | 239.8 | 808.76 |
| 4 | 270.3564 | 414.1982 | 906.19 | 233.5 | 903.17 |
| 6 | 184.4845 | 392.9213 | 1203.42 | 235 | 1570.5 |
| 8 | 183.083 | 319.9174 | 1042.25 | 232.6 | 1805.69 |
| 18 | 47.5226 | 65.3595 | 708.2 | 122.1 | 1998.72 |
| 24 | 15.7984 | 24.462 | 574.35 | 76 | 1523.8 |
| 42 | 0 | 1.7837 | 228.51 | 24 | 1188.98 |
| 48 | 0 | 1.5289 | 52.99 | 7.2 | 878.61 |

The hydrogen sulfide sustained releasing dressings obtained from Examples 1 to 4 could sustain release hydrogen sulfide gas within 24 hours effectively, and the released concentration of hydrogen sulfide did not exceed the safety concentration. Especially, the releasing time of hydrogen sulfide sustained releasing dressing in Examples 2 and 3 could be extended to 48 hours. In contrast, the concentration of the hydrogen sulfide sustained dressing obtained from Comparative Example 1 was higher than 1300 µM in the releasing process. Even though the dressing in Comparative Example 1 released the hydrogen sulfide gas in a longer period of time, the concentration released exceeded the safety concentration.

While the invention has been described by way of example(s) and in terms of the embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A hydrogen sulfide sustained releasing dressing, comprising:
    a hydrocolloid, wherein the hydrocolloid comprises:
        an elastomer, wherein the elastomer is hydrophobic; and
        a hydrophilic polymer, dispersed in the elastomer;
    a surfactant, and sodium hydrosulfide, wherein the sodium hydrosulfide is present at an amount of 0.15 weight percentage to 0.5 weight percentage based on a total weight of the hydrogen sulfide sustained releasing dressing, and the sodium hydrosulfide is cladded by the elastomer.

2. The hydrogen sulfide sustained releasing dressing as claimed in claim 1, wherein the surfactant is polysorbate 80, polysorbate 20, polysorbate 60, or polysorbate 40.

3. The hydrogen sulfide sustained releasing dressing as claimed in claim 1, wherein the hydrocolloid further comprises:
    a tackifier; and
    an extender.

4. The hydrogen sulfide sustained releasing dressing as claimed in claim 3, wherein the elastomer is present at an amount of 10 to 30 parts by weight, the hydrophilic polymer is present at an amount of 20 to 60 parts by weight, the tackifier is present at an amount of 20 to 60 parts by weight, and the extender is present at an amount of 2 to 20 parts by weight.

5. The hydrogen sulfide sustained releasing dressing as claimed in claim 3, wherein the elastomer is selected from the group consisting of styrene-isoprene-styrene (SIS) copolymer, styrene-butadiene-styrene (SBS) copolymer, styrene-(ethylene-butylene)-styrene (SEBS) copolymer and styrene-(ethylene-propylene)-styrene (SEPS) copolymer, and a combination thereof.

6. The hydrogen sulfide sustained releasing dressing as claimed in claim 3, wherein the hydrophilic polymer is selected from the group consisting of sodium carboxymethyl cellulose, hydroxyethyl cellulose, sodium alginate, gelatin, pectin, carboxymethyl chitosan, guar gum, locust bean gum, collagen and karaya gumor, and a combination thereof.

7. The hydrogen sulfide sustained releasing dressing as claimed in claim 3, wherein the tackifier is selected from the group consisting of abietic resin, terpene resin, C5 petroleum resin, C9 petroleum resin and high-purity dicyclopentadiene (H-DCPD), and a combination thereof.

8. The hydrogen sulfide sustained releasing dressing as claimed in claim 3, wherein the extender is selected from the group consisting of mineral oil, liquid paraffin, castor oil, dibutyl phthalate, lanolin and naphthenic oil, and a combination thereof.

9. The hydrogen sulfide sustained releasing dressing as claimed in claim 1, wherein the hydrocolloid further comprises an antioxidant ranging from 0.2 to 2 parts by weight.

10. The hydrogen sulfide sustained releasing dressing as claimed in claim 9, wherein the antioxidant is hindered phenol, thiosynergist, phosphite or secondary aromatic amine.

* * * * *